United States Patent
Etzel et al.

(10) Patent No.: US 11,731,084 B2
(45) Date of Patent: Aug. 22, 2023

(54) DIFFUSION TRANSFER FUNCTIONALIZED MEMBRANE

(71) Applicant: Wisconsin Alumni Research Foundation, Madison, WI (US)

(72) Inventors: Mark Raymond Etzel, Madison, WI (US); Na Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 718 days.

(21) Appl. No.: 16/676,907

(22) Filed: Nov. 7, 2019

(65) Prior Publication Data

US 2020/0147557 A1 May 14, 2020

Related U.S. Application Data

(60) Provisional application No. 62/757,354, filed on Nov. 8, 2018.

(51) Int. Cl.

| | | |
|---|---|---|
| *B01D 67/00* | (2006.01) | |
| *B01D 61/14* | (2006.01) | |
| *B01D 69/02* | (2006.01) | |
| *B01D 71/28* | (2006.01) | |
| *B01D 71/34* | (2006.01) | |
| *B01D 71/68* | (2006.01) | |
| *C07K 1/34* | (2006.01) | |
| *C07K 1/36* | (2006.01) | |

(52) U.S. Cl.
CPC ....... *B01D 67/0088* (2013.01); *B01D 61/145* (2013.01); *B01D 69/02* (2013.01); *B01D 71/28* (2013.01); *B01D 71/34* (2013.01); *B01D 71/68* (2013.01); *C07K 1/34* (2013.01); *C07K 1/36* (2013.01); *B01D 2325/14* (2013.01); *B01D 2325/16* (2013.01)

(58) Field of Classification Search
CPC .... B01D 71/68; B01D 71/34; B01D 67/0088; B01D 2325/14; B01D 2325/16
See application file for complete search history.

(56) References Cited

U.S. PATENT DOCUMENTS

| | | |
|---|---|---|
| 9,688,818 B2 | 6/2017 | Bajjuri et al. |
| 9,868,825 B2 | 1/2018 | Louis et al. |
| 9,968,892 B2 | 5/2018 | Chu et al. |
| 10,068,676 B2 | 9/2018 | Grandjean et al. |
| 2008/0017918 A1 | 1/2008 | Kim |
| 2010/0133172 A1* | 6/2010 | Song ................. C08G 73/0206 525/61 |
| 2011/0147308 A1* | 6/2011 | Johnston-Hall ...... B01D 69/125 210/500.33 |
| 2013/0299428 A1* | 11/2013 | Bikel .................. B01D 67/009 427/244 |

FOREIGN PATENT DOCUMENTS

| | | | |
|---|---|---|---|
| CN | 103 191 649 A | 7/2013 | |
| WO | WO 00/50160 A1 | 8/2000 | |
| WO | WO-2018230786 A1 * | 12/2018 | ............. B01D 63/02 |

OTHER PUBLICATIONS

Abhiram Arunkumar et al., "Fractionation of Glycomacropetide from Whey Using Positively Charged Ultrafiltration Membranes," Foods, vol. 7, No. 10, Oct. 9, 2018 (Oct. 9, 2018), p. 166, XP055679116, CH ISSN: 2304-8158, DOI: 10.3390/foods7100166.
International Preliminary Report on Patentability / Written Opinion, dated May 11, 2021, PCT/US2019/060294.
Hanson, C.M. "Hansen Solubility Parameters: A User's Handbook, Second Edition," © 2007 CRC Press, Boca Raton, Florida: ISBN: 978-0-8493-7248-3 (Book—Copy Not Provided).
Jain et al. (2010) "Protein Purification with Polymeric Affinity Membranes Containing Functionalized Poly(acid) Brushes," *Biomacromolecules*, 11(4):1019-1026.

* cited by examiner

*Primary Examiner* — Ryan B Huang
(74) *Attorney, Agent, or Firm* — Joseph T. Leone; Yanjun Ma; DeWitt LLP

(57) ABSTRACT

A method of making a filter, the resulting filter, and a method of using the filter to filter proteins from solution are described. The method includes contacting a porous, polymeric substrate with a transfer liquid comprising a solvent(s) and a charged polymeric solute. The transfer liquid and the polymeric substrate have a Hansen Solubility Parameter ("HSP") distance of from about 10 to about 35. Contacting the polymeric substrate with the transfer solution causes the polymeric substrate to accept the charged polymeric solute by diffusion transfer, thereby yielding a functionalized filter medium. Removal of the transfer liquid from the polymeric substrate traps the charged polymeric solute on the surface of the polymeric substrate.

31 Claims, No Drawings

DIFFUSION TRANSFER FUNCTIONALIZED MEMBRANE

CROSS-REFERENCE TO RELATED APPLICATIONS

Priority is hereby claimed to provisional application Ser. No. 62/757,354, filed Nov. 8, 2019, which is incorporated herein by reference.

FEDERAL FUNDING STATEMENT

This invention was made with government support awarded under 19-CRHF-0-6055 awarded by the USDA/NIFA. The government has certain rights in the invention.

BACKGROUND

Ultrafiltration is commonly used to concentrate proteins of commercial value from whey. The whey itself is a by-product formed during the making of cheese, Greek yogurt, and other dairy products. Other sources of whey are soy whey left over from making tofu or soy protein isolate. A significant driver in the cost of concentrating the proteins from whey is the price of the ultrafiltration membranes used in the process. Here, a balance must be struck between the molecular weight cut-off value of the filter and the time needed to complete the separation. Using a membrane with a smaller molecular weight cut-off value improves the protein retention of the filter, but it takes a significantly longer amount of time to pass the whey through a tighter filter. Using a membrane with a higher molecular weight cut-off value speeds the process, but also results in protein passing through the membrane into the filtrate, lowering the ultimate protein retention. There thus remains a long-felt and unmet need for protein ultrafiltration membranes that allow for fast flow-through rates, while maintaining high protein retention values.

A host of functionalized filtration membranes are known in the art. These membranes are used in a wide variety of filtration applications, including ion exchange, forward and reverse osmosis, dialysis, gas separation, etc. See, for example, U.S. Pat. No. 10,068,676, issued 4 Sep. 2018, to Grandjean et al., which describes an inorganic, porous filtration membrane functionalized with hexa- and octcya-nometallates. This particular membrane may be used for separating metal cations and solid particles from a liquid medium containing the same. See also U.S. Pat. No. 9,968,892, issued 15 May 2018, to Chu et al., which describes an electrospun nanofibrous filtration material (made from poly-acrylonitrile, polyethersulfone, polyethylene terephthalate, or mixtures thereof), which is then surface modified to contain cross-linked polyethylenimine and polyvinyl amine moieties. This membrane is used to filter bacteria and other similar-sized microorganisms from water.

Functionalized membranes are also known in the field of protein purification. See, for example, Jain et al. (2010) "Protein Purification with Polymeric Affinity Membranes Containing Functionalized Poly(acid) Brushes", *Biomacromolecules*, 11(4):1019-1026. Here, the authors report using porous nylon membranes modified with poly(acid) brushes to purify proteins via a combination of ion-exchange and metal-ion affinity adsorption. The nylon filtration media was functionalized to contain poly(2-(methacryloyloxy)ethyl succinate) ("poly(MES)") "brushes" extending from the surface of the nylon. The poly(MES) brushes where then further functionalized with nitrilotriacetate-$Ni^{2+}$ complexes. The resulting functionalized membranes were capable of binding poly(histidine)-tagged ubiquitin with a capacity of 85±2 mg of protein per $cm^3$ of membrane. These nylon membranes containing functionalized poly(MES) brushes can be used for high-capacity purification of His-tagged proteins from cell extracts.

SUMMARY OF THE INVENTION

Disclosed herein is a method to make an ionically charged filtration membrane or medium. The method starts with a conventional, porous, polymeric substrate. The nominal size of the pores in the substrate is not critical to the fabrication of the filter medium. Typically, however, the pore size should be suitable for filtering proteins from solution. Thus, the pore size of the conventional membrane that serves as the starting material should be based on the nominal molecular weight of the protein(s) desired to be separated, concentrated, or otherwise isolated from a starting solution. Thus, the nominal molecular weight cut-off of the starting substrate will generally run from roughly about 1 kDa to 500,000 kDa or greater.

The porous, polymeric substrate is made to have a net ionic charge by diffusing into it a second, charged polymeric material that imparts an ionic charge, either positive or negative, to the polymeric substrate. This is accomplished by contacting the polymeric substrate with a transfer liquid comprising a solvent and a charged polymeric solute. The charged polymeric solute has an equilibrium affinity for the polymeric substrate but cannot diffuse into the polymeric substrate without the transfer liquid. Contact of the polymeric substrate with the transfer liquid allows the diffusion limitation to be overcome and the charged polymeric solute to transfer into the surface of the polymeric substrate by diffusion. Removal of the transfer liquid traps the charged polymeric solute on the surface of the polymeric substrate.

To facilitate the charged polymeric solute diffusing into the polymeric substrate, the transfer liquid must be capable of swelling the polymeric substrate by at least partially dissolving in the polymeric substrate. Thus, the chosen transfer liquid system and the chosen polymeric substrate should have a Hansen Solubility Parameter ("HSP") distance that enables the charged polymeric solute to diffuse into the polymeric substrate without substantially altering the porosity of the polymeric substrate due to wholescale dissolution of the polymeric substrate in the transfer liquid. The HSP distance can be determined empirically via systematic alteration of the HSP distance. The ideal HSP values can (and do) differ substantially based on the polymeric substrate material, the transfer liquid composition, and the charged polymeric solute chosen. Empirically, this is accomplished by functionalizing a chosen polymeric substrate material as described herein using serial dilutions of the transfer liquid and charged polymeric solute and then testing the resulting functionalized filter media against test solutions of known protein composition and concentration. If a transfer liquid comprises two or more solvents, then proportions of each solvent in the transfer liquid are also tested using serial dilutions to determine the optimum proportions of each individual solvent in the transfer liquid. In this fashion, optimum proportions of the solvent(s) (two or more if a mixed solvent system is used), charged polymeric solute, and time of exposure for any given polymeric substrate material and porosity can be determined without difficulty or undue experimentation. Generally speaking, the HSP distance of the transfer liquid and the polymeric substrate should be from about 10 to about 35. HSP values above and below this range are explicitly within the scope of the method. This enables the transfer liquid to swell the surface of the polymeric substrate without dissolving the polymeric substrate. The transfer liquid (i.e., solvent(s) and charged polymeric solute) is then contacted with the polymeric substrate for a time and at a temperature wherein at least a portion of the charged polymeric solute in the transfer liquid diffuses into the polymeric substrate. The transfer solution is then removed from the polymeric substrate to yield a functionalized filter medium in which the charged polymeric solute has diffused into the polymeric substrate and is presented on the surface of the substrate. Because the charged polymeric solute has a net ionic charge, the polymeric substrate is functionalized to have that same charge (positive or negative).

If the HSP distance is too small between the transfer liquid and the polymeric substrate, the nominal porosity of the substrate might be disadvantageously impacted (typically made larger) because the transfer liquid will dissolve too much of the polymeric substrate. If the HSP distance between the transfer liquid and the polymeric substrate is too large, there will be an insufficient swelling of the polymeric substrate and the dissolved charged polymeric solute will not diffuse to any appreciable amount into the polymeric substrate. In other words, the transfer liquid must simultaneously meet these conditions: (1) it must appreciably swell the polymeric substrate without significantly dissolving it, and (2) it must dissolve the charged polymer without having a higher equilibrium affinity for the charged polymer than does the polymeric substrate. Because charged polymers dissolve well in liquids having a high dielectric constant, such as water, but not well in liquids having a low dielectric constant, such as organic solvents, and because organic solvents are needed to swell organic polymeric substrates, there is a narrow window of charged polymers, transfer liquids, and polymeric substrates for which these conditions are met. That is, outside this window of opportunity, the polymeric substrate will not be functionalized with the charged polymeric solute because diffusion of the charged polymeric solute into the polymeric substrate will not take place to a significant extent.

Thus, disclosed herein is a method of making a filter medium. The method comprises contacting a porous, polymeric substrate with a transfer liquid comprising a solvent(s) and a charged polymeric solute, wherein (i) the transfer liquid and the polymeric substrate have a Hansen Solubility Parameter ("HSP") distance of from about 10 to about 35;

for a time and temperature wherein at least a portion of the charged polymeric solute diffuses into the polymeric substrate;

(ii) removing the transfer liquid from the polymeric substrate to trap the charged polymeric solute on the surface of the polymeric substrate.

As noted earlier, in all versions of the method, the charged polymeric solute may optionally be miscible in the transfer liquid.

The transfer liquid and the polymeric substrate may have an HSP distance of from about 13 to about 32, or from about 18 to about 30, or from about 18 to about 25, or from about 18 to about 20, or any sub-range thereof.

The charged polymeric solute preferably bears a net ionic charge in aqueous solution. The charged polymeric solute may be negatively charged. The negatively charged polymeric solute may (without limitation) comprise a carboxylate or a sulfonate group (or a salt thereof). For example, the charged polymeric solute may comprise a polystyrene sulfonate polymer or co-polymer thereof.

The charged polymeric solute may be a positively charged. The positively charged polymeric solute may be (without limitation) a polymer such as polydiallyldimethylammonium chloride (PDADMAC) or polyhexamethylene biguanide (PHMB) or a co-polymer thereof. The charged polymeric solute may also comprise an amine functionalized styrene-maleic anhydride copolymer or a styrene-maleimide copolymer.

The transfer liquid used may comprise a single solvent or a solvent blend of two or more solvents, one of which may be water. It is typical, but not required, that the solvent(s) be selected from polar aprotic solvents, polar protic solvents, and mixtures therefore. For example, exemplary solvent systems include systems comprising water and a polar aprotic solvent, and water and a different (non-water) polar protic solvent. Polar protic solvents that can be used in the method include, without limitation, water, alcohols (for example, methanol, ethanol, propanol (all isomers) butanol (all isomers), and the like), and carboxylic acids such as formic acid, acetic acid, and the like. Polar aprotic solvents that can be used in the method include (without limitation) dichloromethane, tetrahydrofuran (THF), ethyl acetate, acetonitrile, dimethylformamide (DMF), dimethylacetamide (DMAc), dimethyl sulfoxide (DMSO), acetone, hexamethylphosphoramide (HMPT), and the like.

The polymeric substrate may be any suitably porous polymeric material, without limitation. Polymeric substrates comprising polyethersulfone units or polyvinylidene difluoride are preferred. Likewise, the porosity of the unmodified filter substrate is at the choice of the user based on the material being filtered and the size of the proteins that are desired to be retained by the functionalized filter medium.

Also disclosed herein is the resulting functionalized filter medium made by the method described herein.

Another method disclosed herein is a method of concentrating proteins using the functionalized filter medium description herein. The method comprises adjusting the pH of a solution containing one or more proteins to render the net charge of at least one protein in the solution either positive or negative. That is, the pH of the solution to be passed through the filter is adjusted so that it does not match the net isoelectric point (pI) of the protein desired to be retained by the filter medium. The protein solution is then passed through a filter medium as disclosed herein wherein the filter medium has a net charge that is the same as the net charge of the desired protein in the solution.

DETAILED DESCRIPTION

Abbreviations and Definitions:
 ALA=Alpha-lactalbumin.
 BLG=Beta-lactoglobulin.
 DMAc=dimethylacetamide.
 DMF=Dimethylformamide.
 PDADMAC=Polydiallyldimethylammonium chloride.
 PHMB=Polyhexamethylene biguanide (also known as polyhexanide).
 PES=Polyethersulfone. As used herein PES is synonymous with "polysulfone" ("PSU"), polyarylethersulfone ("PAES"), and poly(arylene sulfone), terms which are in common use in the relevant literature. PES refers generically to polymers having the structure:

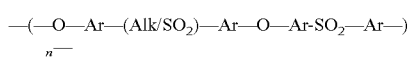

wherein each "Ar" is one or more unsubstituted or substituted $C_6$-, $C_{10}$-, or $C_{14}$-aryl (for example, but not limited to, substituted or unsubstituted phenyl, naphthalenyl, and anthracenyl) or substituted or unsubstituted $C_6$-, $C_{10}$-, or $C_{14}$-heteroaryl wherein the heteroatom(s) is selected from oxygen, nitrogen, or sulfur; substituents on the aryl or heteroaryl ring(s) may include, without limitation, $C_1$-$C_6$-alkyl, halogen, or amine; and "Alk" is a $C_1$-$C_8$ straight or branched alkylenyl or may be absent entirely. PES, for example, includes:

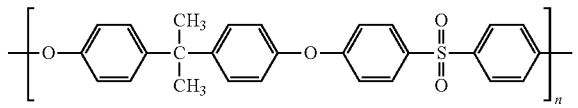

See also, for example, the PES polymers disclosed in U.S. Pat. No. 9,868,825, issued 16 Jan. 2018, to Louis et al. and U.S. Pat. No. 9,688,818, issued 27 Jun. 2017, to Bajjuri et al. A host of PES resins and films are available commercially in a broad range of molecular weights from several international suppliers, including BASF SE, Ludwigshafen, Germany ("ULTRASON"®-brand PES resins) and RTP Company, Winona, Minn.

PSS=Polystyrene sulfonate and salts thereof. PSS polymers have the general structure:

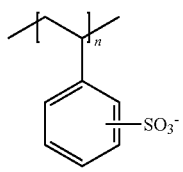

PSS is also available from a large number of commercial suppliers, in a broad range of molecular weights. The sodium salt (CAS No. 25704-18-1), for example, is available from Millipore Sigma, Burlington, Mass.

SMA=Styrene maleic anhydride copolymer and styrene maleimide copolymer and salts thereof:

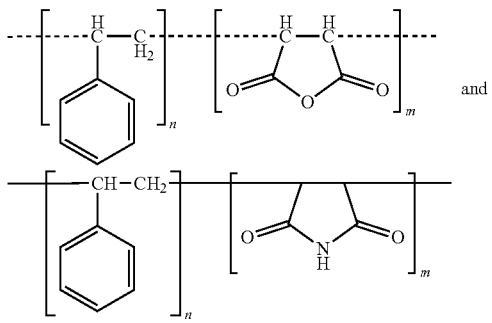

SMA can be made as an alternating copolymer, a random copolymer, or a block copolymer, in a wide range of molecular weights. It is available from several international suppliers, including Sartomer, a wholly owned subsidiary of Arkema (King of Prussia, Pa.), Millipore Sigma, and Cray Valley Company (Houston, Tex.). If the co-polymer contains a maleimide residue, the nitrogen heteroatom may be additionally functionalized. Maleimides also describes a class of derivatives where the NH moiety is replaced with an NR moiety and R is an amine, alkyl or aryl group such as a methyl or phenyl. In the present application, the R moiety is selected to bear an ionic charge in aqueous solution such as a tertiary or quaternary amine or a sulfonate. A short chain alkyl group of from 1 to 15 carbon atoms may serve as a spacer linkage between the charged R moiety and the N atom of the maleimide ring.

HSP=Hansen Solubility Parameter. HSP is an algorithm to predict whether one material will dissolve in another to form a solution. The Hildebrand solubility parameter is the square root of the cohesive energy density of a solvent. Hansen divided the cohesive energy density (CED) into three parts, namely (1) the CED from dispersion forces between molecules; (2) the CED from dipolar intermolecular force between molecules; and (3) the CED from hydrogen bonds between molecules. The HSP is the square root of each of the three values of the CED and is generally measured in $MPa^{1/2}$. The three HSP parameters are then treated as coordinates for a point in three dimensions. The nearer two molecules are in this three-dimensional space, the more likely they are to dissolve into each other. See C. M. Hanson "Hansen Solubility Parameters: A User's Handbook, Second Edition," © 2007 CRC Press, Boca Raton, Fla.; ISBN: 978-0-8493-7248-3.

$L_p$=Hydraulic permeability (also referred to as water flux). Hydraulic permeability is a measure of the flow of water through a filter of given area over time and at a given pressure drop across the filter. Hydraulic permeability values are reported herein in $L/m^2$/hour per bar ("LMH/bar"). The hydraulic permeability ($L_p$) values given in the examples were determined from the slope of the pure water flux ($L/m^2/h$, LMH) versus pressure drop (bar) across the membrane.

$S_o$=observed sieving ratio=$C_P/C_R$, where $C_P$ is the instantaneous concentration of protein that undesirably flows through a given membrane and $C_R$ is the instantaneous concentration of protein that is retained by the membrane. A smaller sieving ratio (i.e., a smaller amount of protein passing through the filter) indicates a more effective filter. For batch filtration systems, $S_o$ values used herein were calculated by mass balance using the equation:

$$S_o = 1 - \frac{\ln[V_F/V_R - (C_P/C_F)(V_F/V_R - 1)]}{\ln(V_F/V_R)}$$

where $V_F/V_R$=the volume ratio of feed solution to retentate, and $C_P/C_F$=the protein concentration ratio of feed solution to permeate. The absorbance ratio at 214 nm or 280 nm ($A_{214}$ or $A_{280}$) was used for $C_P/C_F$, and the volume ratio used was $V_F V_R$=200 mL/100 mL=2.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

The Method of Making the Filter Medium, the Resulting Filter Medium, and Method of Using the Filter Medium:

The method and resulting functionalized filter membranes are best disclosed by way of exemplary working versions of the filter membrane. The following examples are included to provide a more complete description of the functionalized membrane disclosed and claimed herein. The examples do not limit the scope of the claims.

Example 1

Charged membranes were made from 300 kDa pore size raw polyethersulfone (PES) membranes using the charged molecule polystyrene sulfonate (PSS). A 50:50 mixture of dimethylformamide (DMF) in water containing 3.75% (w/v) PSS (poly(sodium 4-styrenesulfonate) Sigma-Aldrich) was contacted with a 76 mm diameter PES membrane disc (Synder Filtration, Vacaville, Calif.) overnight in a stirred cell (400 mL Amicon Stirred Cell, EMD Millipore, Billerica, Mass.) to allow for diffusion transfer, and the membrane then washed with water to remove the DMF and trap the PSS on the membrane. Values of $S_o$ were measured for 1 g/L whey protein isolate (BiPro, Agropur Ingredients, Eden Prairie, Minn.) dissolved in 50 mM sodium phosphate, pH 6.8. The value of the sieving ratio ($S_o$) was calculated by mass balance:

$$S_o = 1 - \frac{\ln[V_F/V_R - (C_P/C_F)(V_F/V_R - 1)]}{\ln(V_F/V_R)}$$

where $V_F/V_R$=the volume ratio of feed solution to retentate, and $C_P/C_F$=the protein concentration ratio of feed solution to permeate. The absorbance ratio at 280 nm ($A_{280}$) was used for $C_P/C_F$, and the volume ratio used was $V_F/V_R$=200 mL/100 mL=2. The hydraulic permeability ($L_p$) was determined from the slope of the pure water flux (L/m²/h, LMH) versus pressure drop (bar) across the membrane.

TABLE 1

Negatively charged ultrafiltration membranes.

| Membrane | $S_o$ | $L_p$ (LMH/bar) |
| --- | --- | --- |
| Water, raw membrane, no PSS | 0.22 | 322 |
| 50% DMF and 75 kDa PSS | 0.015 | 405 |
| 50% DMF and 200 kDa PSS | 0.024 | 338 |
| 50% DMF and 1000 kDa PSS | 0.05 | 410 |

Values of $S_o$ (dimensionless) and $L_p$ (LMH/bar) were measured for each membrane (Table 1). Comparing the unmodified membrane to the one where 75 kDa PSS is trapped, $S_o$ drops more than 14-fold from 0.22 to 0.015 while $L_p$ remains essentially unchanged. Larger molecular-mass PSS (200 and 1,000 kDa) also had a lower value of $S_o$ compared to the raw membrane, but not as low as the 75 kDa PSS. $L_p$ was essentially unaffected by placing a charge on the membrane. This example shows that functionalizing the membrane as described herein resulted in a far more efficient filter medium that still retained filtering speed.

The predominant whey proteins are alpha-lactalbumin (ALA) and beta-lactoglobulin (BLG). They have molecular masses and isoelectric points (pI) of 14.4 kDa and pI 4.4, and 18.4 kDa and pI 5.2, respectively. Proteins have a negative net charge when pH>pI. Therefore, the whey proteins are charged negatively at pH 6.8 and carry the same charge as the charge on the membrane. (Both the proteins and the membrane carry a net negative charge at pH 6.8). This results in electrostatic repulsion of the proteins at the membrane surface. Although the negatively charged proteins are much smaller than the negatively charged pores of the membrane (300 kDa), electrostatic repulsion dominates over size-based filtration to prevent the proteins from passing through the charged membrane pores. The advantage of having wide pore, negatively charged membranes is that both high flux and high protein retention can be obtained simultaneously, something that is not possible without the net negative charge on the membrane.

Furthermore, using the chemistry of Example 1, a finished module containing a raw unmodified membrane can be converted into a charged membrane module in situ simply by pumping suitable functionalizing solutions through the membrane module. Other methods of placing a charge on the membrane use radiation exposure of the membrane itself such as ultraviolet radiation, plasma discharge, or electron beam radiation that initiate free-radical graft polymerization. The present method avoids the complexity, cost, and need to expose the membrane material directly to radiation as with polymer grafting methods. Finished membrane modules have multiple membrane layers either stacked on top of each other or wound around each other and that are encased in a hard membrane housing, all of which prevent exposure of the membrane material uniformly and directly to the incident radiation. These limitations make it problematic to perform radiation-initiated graft polymerization on a finished membrane module. These problems are ameliorated or eliminated entirely using the present method. This is an important advantage of the present method over prior art methods because it allows a membrane manufacturer or membrane user to convert an existing membrane module into a charge-functionalized membrane module without making a new membrane module.

Example 2

Different organic solvents were evaluated for making charged membranes using 75 kDa polystyrene sulfonate (PSS) to examine the metes and bounds of the invention (Table 2). The raw membrane, PSS alone with no organic solvent, and 50% DMF alone with no PSS did not work well. Specifically, values of $S_o$ were not significantly lower than that of the raw membrane. In fact, the 50% DMF alone made the pores of the membrane more open as seen by an 80% increase in $S_o$ and 64% increase in $L_p$. DMF is a good solvent for the membrane polymer PES; coating solutions for the membrane are often made of DMF to completely dissolve the PES and form a clear solution. The 50% DMF treatment probably dissolved some of the membrane material making the pores of the membrane larger. Decreasing the DMF concentration from 50% to 5% made the value of $S_o$ increase 9-fold from 0.0154 to 0.1413 when using 75 kDa PSS.

The Hansen Solubility Parameter (HSP) can explain this. When the solvent and polymer have similar HSP values then the polymer dissolves in it. Each molecule has a total solubility parameter ($\delta_t$) that is divided into three parts: dispersion forces ($\delta_d$), polarization forces ($\delta_p$), and hydrogen bonding forces ($\delta_h$). According to Hansen, the sum of the squares of $\delta_d$, $\delta_p$, and $\delta_h$ equals the square of $\delta_t$. For example, PES has $\delta_d$=19 MPa$^{1/2}$, $\delta_p$=11 MPa$^{1/2}$, and $\delta_h$=8 MPa$^{1/2}$. Another common membrane polymer, polyvinylidene difluoride (PVDF) has $\delta_d$=17 MPa$^{1/2}$, $\delta_p$=12.1 MPa$^{1/2}$, and $\delta_h$=10.2 MPa$^{1/2}$. Water has $\delta_d$=15.5 MPa$^{1/2}$, $\delta_p$=16 MPa$^{1/2}$, and $\delta_h$=42.3 MPa$^{1/2}$, DMF has $\delta_d$=17.4 MPa$^{1/2}$, $\delta_p$=13.7 MPa$^{1/2}$, and $\delta_h$=11.3 MPa$^{1/2}$. Solvent blends are handled by using the volume ratio of the solvents to calculate each of the three parts of the solubility parameter of the mixture.

The HSP distance (Ra), is calculated using the equation:

$$(Ra)^2 = 4(\delta_{d2}-\delta_{d1})^2 + (\delta_{p2}-\delta_{p1})^2 + (\delta_{h2}-\delta_{h1})^2$$

for the solvent blend and polymer system. For example, the water and PES system, $$(Ra)^2 = 4(15.5-19)^2 + (16.0-11)^2 + (42.3-8)^2 = 1250$$

has an HSP distance of Ra=35.4. The smaller the HSP distance the better the solvent is for the polymer. As the HSP distance decreases, the polymer is swollen more by the solvent and eventually dissolves in the solvent. Table 2 lists the HSP distance for different combinations of PES and solvent, and the measured values of $S_o$ and $L_p$ for that combination.

TABLE 2

| Solvent | $S_o$ | $L_p$ (LMH/bar) | HSP distance |
|---|---|---|---|
| Water, raw membrane, no PSS | 0.2169 | 322 | 35.4 |
| Water, PSS alone, no DMF | 0.1961 | 283 | 35.4 |
| 50% DMF alone, no PSS | 0.3904 | 529 | 19.9 |
| 50% DMF and PSS | 0.0154 | 405 | 19.9 |
| 30% DMF and PSS | 0.0887 | 261 | 26.0 |
| 20% DMF and PSS | 0.0903 | 245 | 29.1 |
| 10% DMF and PSS | 0.0907 | 286 | 32.2 |
| 5% DMF and PSS | 0.1413 | 273 | 33.8 |
| 50% tert-butyl alcohol and PSS | 0.0427 | 481 | 21.8 |
| 50% ethanol and PSS | 0.0183 | 437 | 23.9 |
| 10% ethanol and PSS | 0.2333 | 245 | 33.0 |
| 50% acetone and PSS | 0.0763 | 450 | 18.2 |
| 50% DMF and PVSA | 0.38 | 665 | 19.9 |

Decreasing the DMF concentration from 50% to 5% made the HSP distance increase from 19.9 to 33.8. The 9-fold increase in the value of $S_o$ is attributed to the increase in the HSP distance as the DMF concentration goes from 50% to 5%. Without being limited to any underlying mechanism or phenomenon, the hypothesis is that the PES polymer is made more receptive to diffusion transfer of the charged polymer from the solvent blend onto and/or into the membrane surface. For example, when the HSP distances for water, 5% DMF, and 10% ethanol exceeded about 33, then the PSS did not function ideally. Whereas when the HSP distance was less than about 30 the functionalized PSS worked very well indeed, and when the HSP distance was less than about 25 then the values of $S_o$ were the lowest.

HSP can be too small. For example, the HSP distance between 100% DMF and PES is only 5.3. Thus, the PES membrane dissolves completely in 100% DMF. Furthermore, when the HSP distance is too small, the solvent blend may be too hydrophobic to dissolve the charged polymer. The charged polymer must at least be slightly soluble in the solvent blend. Charged polymers are hydrophilic due to the charged moieties being anions or cations. Charged polymers are often not soluble in anhydrous organic solvents that have low dielectric constants compared to water. The dielectric constant of water is higher than that of most organic solvents. Adding water to the solvent blend solvates the charged polymer and prevents dissolution of the membrane polymer in the solvent blend. However, adding water to the solvent blend adds another constraint on the organic solvent: the organic solvent must have significant solubility with water.

Another desirable feature when choosing a charged polymer/solvent blend/membrane polymer system is to have a greater equilibrium affinity between the charged polymer and the membrane polymer than between the charged polymer and the solvent blend. This is illustrated by the last entry in Table 2 where the charged polymer polyvinylsulfonic acid (PVSA) in 50% DMF failed to lower $S_o$ compared to 50% DMF alone. The difference between PVSA, which failed to lower $S_o$ compared to 50% DMF alone, and PSS which did lower $S_o$ by 25-fold compared to 50% DMF alone, is that PVSA has no phenyl moiety in the polymer backbone. The phenyl moiety in the PES polymer backbone creates a thermodynamic affinity between the PSS and the PES. This affinity is the driving force for diffusion transfer of the charged polymer into the membrane polymer. PVSA did not have that affinity and did not work.

The PVSA example illustrates a fundamental feature of the method disclosed herein wherein the transfer liquid has to meet tight constraints. The transfer liquid must dissolve the charged polymer and make the membrane polymer receptive to diffusion transfer. If the transfer liquid contains too much organic solvent, then the HSP distance is too small, and the transfer liquid dissolves the membrane polymer. In addition, in this situation, the charged polymer may not dissolve well in the transfer liquid, because the charged polymer is ionically charged. If the transfer liquid contains too little organic solvent, then the membrane polymer is not sufficiently receptive to diffusion transfer. For example, the PVSA did not dissolve in 50% DMF at either 3.75% or 1.875% concentration. To solve this problem, the 50% DMF was acidified to pH 0.8 by addition of HCl to protonate the sulfonic acid moiety, making the PVSA soluble at 1.875% concentration, but not at 3.75%. In this way, the transfer liquid could both dissolve the charged polymer and contain enough organic solvent to make the membrane polymer receptive to diffusion transfer.

In summary, the method disclosed herein solves these problems by creating a soluble mixture, the transfer liquid, that dissolves the charged solute polymer, is similar in HSP to the membrane substrate polymer (without dissolving it wholescale) and makes the membrane polymer receptive to diffusion transfer of the charged polymer. When the HSP distance between the transfer liquid and the membrane polymer is too large then the polymeric substrate is not sufficiently functionalized. Without being tethered to any underlying mechanism or phenomenon, the current understanding is that as the HSP distance increases, the transfer liquid becomes a poor solvent for the polymeric substrate. This prevents the filter substrate from being receptive to the charged polymer; the charged polymer cannot diffuse into the polymeric substrate. Conversely, when the HSP distance is too small then the membrane polymer dissolves in the transfer liquid. Additionally, the charged polymeric solute might not have sufficient solubility in the transfer liquid. In that instance, the substrate dissolves too quickly and the charged polymeric solute is not sufficiently soluble in the solvent (or solvent system) to rise to a concentration high enough to initiate diffusion in the membrane substrate. Lastly, it is important that the charged polymer has a greater affinity for the membrane polymer than for the transfer liquid in order to provide a driving force for diffusion transfer of the charged polymer from the transfer liquid into the membrane polymer.

Example 3

Positively charged PES ultrafiltration membranes were made by adaptation of the procedure in Example 1. Whey protein solution was adjusted to pH 3.5 to make the net charge on the proteins positive. Positively charged polymers examined were 100-200 kDa polydiallyldimethylammonium chloride (PDADMAC), and 1.75-2.20 kDa polyhexamethylene biguanide (PHMB).

Comparing the unmodified membrane to the one where PDADMAC is trapped using 50% DMF, $S_o$ drops about 5.8-fold from 0.37 to 0.064 while $L_p$ remains essentially unchanged (Table 3). For PDADMAC in 50% ethanol, $S_o$ drops about 7.5-fold from 0.37 to 0.049 and $L_p$ remains essentially unchanged. For PDADMAC in water, $S_o$ drops about 2.7-fold from 0.37 to 0.136, and $L_p$ drops by about 1.7-fold. When $L_p$ drops it means that the membrane pores got tighter. Tighter pores alone decrease $S_o$ regardless of the effect of the charge placed on the membrane by the PDADMAC. The fact that PDADMAC in water worked at all was attributed both to tighter pores of the membrane and the hydrophobicity of the repeating pyrrolidine ring moiety incorporated into the polymer backbone. An affinity between the pyrrolidine ring of the PDADMAC and the phenyl ring of the PES may have facilitated trapping of the PDADMAC in the PES membrane using water. Nevertheless, PDADMAC in 50% ethanol not 100% water worked the best of the combinations tested.

Comparing the unmodified membrane to the one where PHMB is trapped using 50% DMF, $S_o$ drops about 2.4-fold from 0.37 to 0.15 while $L_p$ increases by about 45%. The PHMB was small, (~2 kDa) compared to the PDADMAC (~150 kDa). Furthermore, PHMB lacked the hydrophobic ring moiety of the PDADMAC. The observation that PDADMAC worked better than PHMB was attributed to these factors.

In summary, positively charged PES membranes were made successfully using the present method. Furthermore, the importance of the charged polymer having some hydrophobic and some hydrophilic molecular character was affirmed, as was the importance of the solvent blend having a small enough HSP distance to trap the charged polymer on the membrane.

TABLE 3

| Solvent | $S_o$ | $L_p$ (LMH/bar) | HSP distance |
| --- | --- | --- | --- |
| Water, raw membrane | 0.3693 | 315 | 35.4 |
| 50% DMF alone | 0.6830 | 656 | 19.9 |
| 50% DMF and PDADMAC | 0.0643 | 318 | 19.9 |
| 50% ethanol and PDADMAC | 0.0487 | 357 | 23.9 |
| Water and PDADMAC | 0.1357 | 189 | 35.4 |
| 50% DMF and PHMB | 0.1533 | 458 | 19.9 |

Example 4

Styrene maleic anhydride copolymer (SMA) comprises repeating styrene and maleic anhydride moieties in the polymer backbone. The relative frequency of the moieties can be altered which alters the prevalence of the hydrophobic phenyl moiety mentioned in Example 3. The reactive maleic anhydride moiety can be made either charged positive or negative. For example, hydrolysis of the maleic anhydride moiety makes two carboxylic acids that are charged negative. Alternatively, reaction of the maleic anhydride moiety with dimethylaminopropylamine forms a tertiary amine moiety. Thus, SMA is a generic polymer for use in the present invention because it can make either a positive or a negative ultrafiltration membrane.

A positively charged PES ultrafiltration membrane was made using a tertiary amine derivative of SMA (SMA-1000I, Cray Valley Company, Houston, Tex.). SMA-1000I is a 5 kDa copolymer of styrene and dimethylaminopropylamine maleimide. The positively charged membrane was made by adaptation of the procedure in Example 1. Whey protein solution was adjusted to pH 3.5 to make the net charge on the proteins positive.

TABLE 4

Positively charged SMA ultrafiltration membranes.

| Membrane | $S_o$ | $L_p$ (LMH/bar) | HSP distance |
| --- | --- | --- | --- |
| Water, raw membrane | 0.3693 | 315 | 35.4 |
| 100% ethanol alone | 0.4943 | 477 | 13.3 |
| 100% ethanol and SMA-1000I | 0.0730 | 293 | 13.3 |

Comparing the unmodified membrane to the one where the SMA-1000I is trapped using 100% ethanol, $S_o$ drops about 5.1-fold from 0.37 to 0.073 while $L_p$ remains essentially unchanged (Table 4). The HSP distance of 100% ethanol was large enough to not dissolve the PES membrane and yet it dissolved the SMA-1000I completely. Furthermore, the HSP distance of 100% ethanol is 13.3, smaller than for 50% DMF (HSP=19.9). This smaller HSP distance makes the surface of the PES membrane more receptive to diffusion transfer of the SMA-1000I than the 50% DMF. After the SMA-1000I is fixed to the surface of the membrane by diffusion transfer, the membrane is washed with water (HSP=35.4), which reverses the receptivity of the membrane surface to diffusion transfer ensuring that the SMA1000I will not wash off with water. In this way the SMA-1000I is trapped on the surface of the membrane. Because protein separations are conducted in aqueous solution, it is important that the SMA-1000I charged polymer sticks to the membrane surface and not wash off with water.

A negatively charged PES ultrafiltration membrane was made using hydrolyzed SMA (SMA 1000 HNa, Cray Valley, Houston, Tex.). Both the SMA-1000I and hydrolyzed SMA (SMA-COO$^-$) were made from the same unreacted SMA (SMA 1000, 5kDa, Cray Valley) that comprises styrene and maleic anhydride moieties in a 1:1 molecular ratio. Hydrolyzed SMA was dissolved in 50% DMF. The 50% DMF solution was acidified by addition of 1 M HCl prior to the diffusion transfer step to protonate the carboxylic acids and make the hydrolyzed SMA soluble in 50% DMF. The membrane was then washed with 0.1 M NaOH in water to deprotonate the carboxylic acids and form anions that make the hydrolyzed SMA water soluble. The water wash step removes any free hydrolyzed SMA not trapped on the membrane surface by the diffusion transfer step. The water wash step also removes the solvent mixture from the membrane surface reversing the receptivity of the membrane surface to diffusion transfer of the charged polymer. This process sticks the charged polymer onto the membrane surface so that the charged polymer will not wash off with water. Whey protein solution was adjusted to pH 6.8 to make the net charge on the proteins negative like the membrane.

TABLE 5

Negatively charged SMA ultrafiltration membranes.

| Membrane | $S_o$ | $L_p$ (LMH/bar) | HSP distance |
|---|---|---|---|
| Water, raw membrane | 0.2169 | 322 | 35.4 |
| 50% DMF alone | 0.3904 | 529 | 19.9 |
| 50% DMF and SMA-COO⁻ (1.875%) | 0.074 | 458 | 19.9 |
| 50% DMF and SMA-COO⁻ (3.75%) | 0.037 | 436 | 19.9 |
| Back extraction of 50% DMF and SMA-COO⁻ (3.75%) | 0.011 | 306 | 19.9 |
| 50% DMAc alone | 0.3260 | 646 | 19.3 |
| 50% DMAc and SMA-COO⁻ (3.75%) | 0.0363 | 341 | 19.3 |

Two different concentrations of SMA-COO⁻ were evaluated (Table 5). Comparing the unmodified (raw) membrane to the one where the SMA-COO⁻ is trapped using 50% DMF, $S_o$ drops about 3-fold for 1.875% SMA-OOO⁻ from 0.22 to 0.074, and about 6-fold for 3.75% SMA-COO⁻ from 0.22 to 0.037, while $L_p$ increased about 1.4-fold at both SMA-COO⁻ concentrations.

Back extraction of the 3.75% SMA-COO⁻ membrane using 50% DMF was attempted to learn if the SMA-COO⁻ washes off the membrane. This did not happen. After 16 h of back extraction in 50% DMF, the value of $S_o$ did not increase. This result was attributed to the greater equilibrium affinity of the phenyl ring of the SMA-COO⁻ for the phenyl ring of the PES than for the 50% DMF solvent blend. At equilibrium, the SMA-COO⁻ prefers to partition into the PES polymer rather than into the 50% DMF solvent blend that is half water. Based on the back-extraction result, two mechanisms may trap the charged polymer onto the surface of the polymeric membrane. First, the water wash step removes the solvent mixture from the membrane surface reversing the receptivity of the membrane polymer to diffusion transfer. Second, the charged polymer has a higher equilibrium affinity for the membrane polymer than for either the wash water or the diffusion transfer solvent. The equilibrium affinity attraction and the halting the diffusion transfer process together help stick the charged polymer onto the membrane surface so that the charged polymer does not wash off.

The organic solvent dimethylacetamide (DMAc) is commonly used to dissolve PES during the membrane manufacturing process. Because this solvent is commonly present in manufacturing, it was tested for suitability in the diffusion transfer process. As shown in Table 5, comparing the unmodified (raw) membrane to the one where the SMA-COO⁻ at 3.75% concentration is trapped using either 50% DMF or 50% DMAc, the value of $S_o$ drops about 6-fold for both transfer liquids. DMAc worked as well as DMF in the method disclosed herein. This result was attributed to the similar HSP distances for 50% DMF (Ra=19.9) and 50% DMAc (Ra=19.3) as shown in Table 5.

In summary, SMA was successfully used to make negatively charged and positively charged PES ultrafiltration membranes using the present invention. The SMA used to make both membranes contained styrene and maleic anhydride moieties in a 1:1 molecular ratio. This illustrates the feature of the present method that the charged polymer has some hydrophobic and some hydrophilic molecular character. The positively charged membrane was made using a tertiary amine derivative of SMA and the negatively charged membrane was made using a carboxylate version of the SMA. This example illustrates that the present method works to make a charged ultrafiltration membrane by the diffusion transfer method starting with a polymer that has a hydrophobic phenyl moiety in the polymer backbone and a second hydrophilic moiety that is either charged positive or negative. The generic aspect of this SMA example is that copolymers containing some hydrophobic and some hydrophilic molecular character to make diffusion transfer functionalized membranes that are charged and that substantially decrease the sieving coefficients of proteins.

Example 5

Polyvinylidene difluoride (PVDF) is another common polymer, like PES, used to make ultrafiltration membranes. Following the methods of Example 1, negatively charged membranes were made using 250 kDa pore size raw PVDF membranes (Synder Filtration, Vacaville, Calif.) and either 75 kDa PSS or 5 kDa SMA-COO⁻.

TABLE 6

Negatively charged PVDF ultrafiltration membranes.

| Membrane | $S_o$ | $L_p$ (LMH/bar) | HSP distance |
|---|---|---|---|
| Water, raw membrane | 0.5528 | 270 | 32.5 |
| 50% DMF alone | 0.4263 | 149 | 16.9 |
| 50% DMF and PSS | 0.1547 | 156 | 16.9 |
| 50% DMF and SMA-COO⁻ (1.875%) | 0.1703 | 242 | 16.9 |

As shown in Table 6, comparing the unmodified (raw) PVDF membrane to the one where PSS is trapped on the surface of the membrane using 50% DMF, $S_o$ drops about 3.6-fold from 0.55 to 0.15, while $L_p$ drops about 1.7-fold. For SMA-COO⁻, $S_o$ drops about 3.2-fold from 0.55 to 0.17, while $L_p$ drops about 1.1-fold. Thus, the method disclosed herein also works for PVDF polymeric membranes.

This success can be explained using the principles described above. First, the HSP distances for 50% DMF and the membrane polymers are similar: Ra=19.9 for PES and Ra=16.9 for PVDF. These values are both well within the HSP distance of about 10 to about 35 recommended for the diffusion transfer process. Second, as shown in Table 7, the HSP values are similar for PES and PVDF. Thus, although PVDF does not have the phenyl rings of PES, the difluoroethyl repeating moiety of PVDF is hydrophobic. Because the charged polymers PSS and SMA-COO⁻ both contain phenyl rings that are hydrophobic, this creates an equilibrium affinity between the charged polymer and the hydrophobic membrane polymers PES and PVDF.

TABLE 7

HSP parameters in units of MPa$^{1/2}$ for PES and PVDF.

| | $\delta_d$ | $\delta_p$ | $\delta_h$ | $\delta_t$ |
|---|---|---|---|---|
| PES | 19 | 11 | 8 | 23 |
| PVDF | 17 | 12.1 | 10.2 | 23 |

What is claimed is:

1. A method of making a filter, the method comprising:
   (a) contacting a raw unmodified porous, polymeric substrate with a transfer liquid comprising at least one solvent and a charged polymeric solute, wherein the transfer liquid and the polymeric substrate have a Hansen Solubility Parameter ("HSP") distance of from about 10 to about 35, for a time and at a temperature wherein at least a portion of the charged polymeric solute diffuses into the polymeric substrate; and then
   (b) removing the transfer liquid from the polymeric substrate to trap the portion of the charged polymeric solute that diffuses into the polymeric substrate in step (a) on the surface of the polymeric substrate.

2. The method of claim 1, wherein the transfer liquid and the polymeric substrate have a HSP distance of from about 10 to about 32.

3. The method of claim 1, wherein the transfer liquid and the polymeric substrate have a HSP distance of from about 13 to about 30.

4. The method of claim 1, wherein the transfer liquid and the polymeric substrate have a HSP distance of from about 13 to about 25.

5. The method of claim 1, wherein the transfer liquid and the polymeric substrate have a HSP distance of from about 13 to about 20.

6. The method of claim 1, wherein the at least one solvent is selected from the group consisting of a polar aprotic solvent, a polar protic solvent, mixtures comprising water and a polar aprotic solvent, and water and a non-aqueous polar protic solvent.

7. The method of claim 1, wherein the at least one solvent is selected from the group consisting of dimethylacetamide ("DMAc"), dimethylformamide ("DMF"), ethanol, mixtures of DMAc and water, mixtures of DMF and water, and mixtures of ethanol and water.

8. The method of claim 1, wherein the polymeric substrate is a polyethersulfone or a polyvinylidene difluoride.

9. The method of claim 1, wherein the charged polymeric solute is miscible in the transfer liquid.

10. The method of claim 9, wherein the transfer liquid and the polymeric substrate have a HSP distance of from about 10 to about 32.

11. The method of claim 9, wherein the transfer liquid and the polymeric substrate have a HSP distance of from about 13 to about 30.

12. The method of claim 9, wherein the transfer liquid and the polymeric substrate have a HSP distance of from about 13 to about 25.

13. The method of claim 9, wherein the transfer liquid and the polymeric substrate have a HSP distance of from about 13 to about 20.

14. The method of claim 9, wherein the at least one solvent is selected from the group consisting of a polar aprotic solvent, a polar protic solvent, mixtures comprising water and a polar aprotic solvent, and water and a non-aqueous polar protic solvent.

15. The method of claim 9, wherein the at least one solvent is selected from the group consisting of DMAc, DMF, ethanol, mixtures of DMAc and water, mixtures of DMF and water, and mixtures of ethanol and water.

16. The method of claim 9, wherein the polymeric substrate is a polyethersulfone or a polyvinylidene difluoride.

17. The method of claim 1, wherein the charged polymeric solute is negatively charged.

18. The method of claim 17, wherein the charged polymeric solute comprises a sulfone or a sulfonate group.

19. The method of claim 17, wherein the charged polymeric solute is a polystyrene sulfonate.

20. The method of claim 17, wherein the at least one solvent is selected from the group consisting of a polar aprotic solvent, a polar protic solvent, mixtures comprising water and a polar aprotic solvent, and water and a non-aqueous polar protic solvent.

21. The method of claim 17, wherein the at least one solvent is selected from the group consisting of DMAc, DMF, ethanol, mixtures of DMAc and water, mixtures of DMF and water, and mixtures of ethanol and water.

22. The method of claim 17, wherein the polymeric substrate is a polyethersulfone or a polyvinylidene difluoride.

23. The method of claim 1, wherein the charged polymeric solute is positively charged.

24. The method of claim 23, wherein the charged polymeric solute is selected from the group consisting of polydiallyldimethylammonium chloride and polyhexamethylene biguanide.

25. The method of claim 23, wherein the at least one solvent is selected from the group consisting of a polar aprotic solvent, a polar protic solvent, mixtures comprising water and a polar aprotic solvent, and water and a non-aqueous polar protic solvent.

26. The method of claim 23, wherein the at least one solvent is selected from the group consisting of DMAc, DMF, ethanol, mixtures of DMAc and water, mixtures of DMF and water, and mixtures of ethanol and water.

27. The method of claim 23, wherein the polymeric substrate is a polyethersulfone or a polyvinylidene difluoride.

28. The method of claim 1, wherein the charged polymeric solute comprises a styrene-maleic anhydride copolymer or a styrene-maleimide copolymer.

29. The method of claim 28, wherein the at least one solvent is selected from the group consisting of a polar aprotic solvent, a polar protic solvent, mixtures comprising water and a polar aprotic solvent, and water and a non-aqueous polar protic solvent.

30. The method of claim 28, wherein the at least one solvent is selected from the group consisting of DMAc, DMF, ethanol, mixtures of DMAc and water, mixtures of DMF and water, and mixtures of ethanol and water.

31. The method of claim 28, wherein the polymeric substrate is a polyethersulfone or a polyvinylidene difluoride.

* * * * *